(12) United States Patent
McCarthy et al.

(10) Patent No.: US 9,237,895 B2
(45) Date of Patent: Jan. 19, 2016

(54) SURGICAL AIMER

(71) Applicant: Smith & Nephew, Inc., Memphis, TN (US)

(72) Inventors: Gary R. McCarthy, East Bridgewater, MA (US); Michael C. Ferragamo, Foster, RI (US); Susan L. Spear, Pawtucket, RI (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/461,965

(22) Filed: Aug. 18, 2014

(65) Prior Publication Data

US 2014/0350562 A1  Nov. 27, 2014

Related U.S. Application Data

(63) Continuation of application No. 12/340,896, filed on Dec. 22, 2008, now Pat. No. 8,840,604.

(60) Provisional application No. 61/015,907, filed on Dec. 21, 2007.

(51) Int. Cl.
*A61B 17/17* (2006.01)
*A61B 1/32* (2006.01)
*A61B 17/00* (2006.01)

(52) U.S. Cl.
CPC .............. *A61B 17/1714* (2013.01); *A61B 1/32* (2013.01); *A61B 2017/0046* (2013.01); *A61B 2017/00469* (2013.01)

(58) Field of Classification Search
CPC .................................. A61B 17/28; A61B 1/32
USPC ....................... 606/88, 96, 102; 600/210, 213
See application file for complete search history.

(56) References Cited

U.S. PATENT DOCUMENTS

| | | |
|---|---|---|
| 2,475,896 A | 7/1949 | Husted |
| 3,672,419 A | 6/1972 | Fischer |
| 4,559,456 A | 12/1985 | Yamamoto et al. |
| 4,763,548 A | 8/1988 | Leibinger et al. |
| 5,112,335 A | 5/1992 | Laboureau et al. |
| 5,300,077 A | 4/1994 | Howell |
| 5,320,115 A | 6/1994 | Kenna |
| 5,320,626 A | 6/1994 | Schmieding |
| 5,374,269 A | 12/1994 | Rosenberg |

(Continued)

FOREIGN PATENT DOCUMENTS

| | | |
|---|---|---|
| EP | 1329197 A1 | 7/2003 |
| GB | 2268688 A | 1/1994 |

(Continued)

OTHER PUBLICATIONS

International Search Report and Written Opinion for PCT/US2008/087933, May 27, 2009.

(Continued)

*Primary Examiner* — William Thomson
*Assistant Examiner* — Victor Shapiro
(74) *Attorney, Agent, or Firm* — Burns & Levinson LLP; Joseph M. Maraia (57) ABSTRACT

The present disclosure relates to a surgical aimer including a shaft having a proximal portion and a distal portion and a handle coupled to the proximal portion of the shaft. The handle includes a mechanism for coupling the shaft to the handle and releasing the shaft from the handle.

21 Claims, 12 Drawing Sheets

(56) References Cited

U.S. PATENT DOCUMENTS

| | | |
|---|---|---|
| 5,520,693 A | 5/1996 | McGuire |
| 5,788,701 A | 8/1998 | McCue |
| 5,968,050 A | 10/1999 | Torrie |
| 6,120,511 A | 9/2000 | Chan |
| 6,783,516 B2 | 8/2004 | O'Heeron et al. |
| 6,824,003 B1 | 11/2004 | Wong |
| 7,025,770 B2 | 4/2006 | McGuire et al. |
| 7,976,555 B2 | 7/2011 | Meade |
| 2002/0077530 A1 | 6/2002 | Velikaris et al. |
| 2003/0195392 A1 | 10/2003 | Hamel et al. |
| 2003/0229344 A1 | 12/2003 | Dycus et al. |
| 2004/0116843 A1 | 6/2004 | Chan |
| 2005/0228398 A1 | 10/2005 | Rathbun et al. |
| 2006/0106398 A1 | 5/2006 | Lauryssen et al. |
| 2007/0233150 A1 | 10/2007 | Blain et al. |

FOREIGN PATENT DOCUMENTS

| | | |
|---|---|---|
| WO | 0249521 A1 | 6/2002 |
| WO | 2008064211 A1 | 5/2008 |

OTHER PUBLICATIONS

International Search Report and Written Opinion for PCT/US2010/034328, Jul. 29, 2010.

International Search Report and Written Opinion for PCT/US2010/034328, Jan. 5, 2012.

Australian Examination Report No. 1 for Australian Patent Application No. 2008345557, date of issue Feb. 27, 2013 (Note references D1 & D2 previously identified by Applicants).

Communication pursuant to Article 94(3) EPC for related European Application No. 08868074.9 dated Oct. 15, 2015.

SURGICAL AIMER

CROSS REFERENCE TO RELATED APPLICATIONS

This application is a continuation of U.S. patent application Ser. No. 12/340,896 filed Dec. 22, 2008 entitled SURGICAL AIMER, which claims benefit of the priority of U.S. Provisional Patent Application No. 61/015,907 filed Dec. 21, 2007 entitled SURGICAL AIMER.

BACKGROUND

1. Field of Technology

The present disclosure relates to a surgical aimer, and more particularly, to a surgical aimer having a handle configured to allow a surgeon the option of an in-line or pistol grip aimer position during a ligament reconstruction procedure.

2. Related Art

When a ligament or tendon becomes detached from the bone, surgery is usually required to re-secure the ligament or tendon. Often a substitute ligament or graft is attached to the bone to facilitate re-growth and permanent attachment. The reattachment procedure involves drilling of a graft tunnel between two bones, for example, the tibia and the femur.

To achieve optimal results, it is important that the graft tunnel be drilled at a particular angle and location through the tibia and femur. Ordinarily an incision is made to access the proper area for drilling a tunnel through the tibia. A guide pin is placed through the incision and driven into the tibia. A drill is then placed over and guided by the guide pin during the drilling of the graft tunnel through the tibia.

A problem arises in locating the proper position for drilling the graft tunnel in the femur. For proper alignment of a drill guide for drilling a graft tunnel in a femur, an endoscopic drill guide including a shaft with an offset hook has been used. These drill guides allow for in-line and pistol grip positioning of the shaft relative to the handle, but the mechanisms for mounting and locking of the shaft are cumbersome.

An endoscopic drill guide that allows for easy mounting and locking of the shaft, in either an in-line or pistol grip position, is needed.

SUMMARY

In one aspect, the present disclosure relates to a surgical aimer including a shaft having a proximal portion and a distal portion and a handle coupled to the proximal portion of the shaft. The handle includes a mechanism for coupling the shaft to the handle and releasing the shaft from the handle. In an embodiment, the mechanism includes a stationary member and a movable member slidably engaged with the stationary member. In another embodiment, the stationary member includes a spring, wherein the movable member is spring-loaded against the stationary member. In yet another embodiment, the movable member includes a locking portion. In a further embodiment, the locking portion is engaged with the proximal portion of the shaft when the locking portion is located in a first position and unengaged with the proximal portion of the shaft when the locking portion is located in a second position.

In yet a further embodiment, the mechanism is transverse to a longitudinal axis of the handle. In an embodiment, the handle includes a first channel configured for disposal of the shaft and configured for disposal of the shaft. In another embodiment, the first channel is parallel with a longitudinal axis of the handle and the second channel is located at an angle relative to the first channel. In yet another embodiment, the shaft is parallel with a longitudinal axis of the handle when the shaft is disposed within the first channel. In a further embodiment, the shaft is located at an angle relative to a longitudinal axis of the handle when the shaft is disposed within the second channel. In yet a further embodiment, the handle includes a first pin for aligning the shaft within the handle when the shaft is disposed within the first channel and a second pin for aligning the shaft within the handle when the shaft is disposed within the second channel.

In an embodiment, the distal portion of the shaft includes a tip that is offset at an angle relative to the shaft. In another embodiment, the tip is positioned above the shaft. In yet another embodiment, the tip is positioned below the shaft. In a further embodiment, the handle includes a first cover slidably coupled to the handle and a second cover slidably coupled to the handle. In yet a further embodiment, the first cover is configured for extending over the second channel and the second cover is configured for extending over the first channel. In an embodiment, both the first cover and the second cover includes a body and an actuating portion.

In another aspect, the present disclosure relates to a surgical aimer handle including a mechanism configured for coupling and uncoupling the shaft to the handle. In an embodiment, the mechanism includes a stationary member and a movable member, wherein the movable member is slidably engaged with the stationary member. In another embodiment, the stationary member includes a spring, wherein the movable member is spring-loaded against the stationary member. In yet another embodiment, the movable member includes a locking portion. In a further embodiment, the locking portion is engaged with a proximal portion of the shaft when the locking portion is located in a first position and unengaged with a proximal portion of the shaft when the locking portion is located in a second position.

In yet a further embodiment, the mechanism is transverse to a longitudinal axis of the handle. In an embodiment, the handle includes a first channel configured for disposal of the shaft and a second channel configured for disposal of the shaft. In another embodiment, the first channel is parallel with a longitudinal axis of the handle and the second channel is located at an angle relative to the first channel. In yet another embodiment, the shaft is parallel with a longitudinal axis of the handle when the shaft is disposed within the first channel. In a further embodiment, the shaft is located at an angle relative to a longitudinal axis of the handle when the shaft is disposed within the second channel. In yet a further embodiment, the handle includes a first pin for aligning the shaft within the handle when the shaft is disposed within the first channel and a second pin for aligning the shaft within the handle when the shaft is disposed within the second channel.

In an embodiment, a distal portion of the shaft includes a tip that is offset at an angle relative to the shaft. In another embodiment, the tip is positioned above the shaft. In yet another embodiment, the tip is positioned below the shaft. In yet another embodiment, the handle includes a first cover slidably coupled to the handle and a second cover slidably coupled to the handle. In a further embodiment, the first cover is configured for extending over the second channel and the second cover is configured for extending over the first channel. In yet a further embodiment, both the first cover and the second cover includes a body and an actuating portion.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION

The disclosures of U.S. patent application Ser. No. 12/340,896 filed Dec. 22, 2008 entitled SURGICAL AIMER, and U.S. Provisional Patent Application No. 61/015,907 filed Dec. 21, 2007 entitled SURGICAL AIMER, are hereby incorporated herein by reference in their entirety.

The following description of the preferred embodiment(s) is merely exemplary in nature and is in no way intended to limit the disclosure, its application, or uses.

Figure 1A:
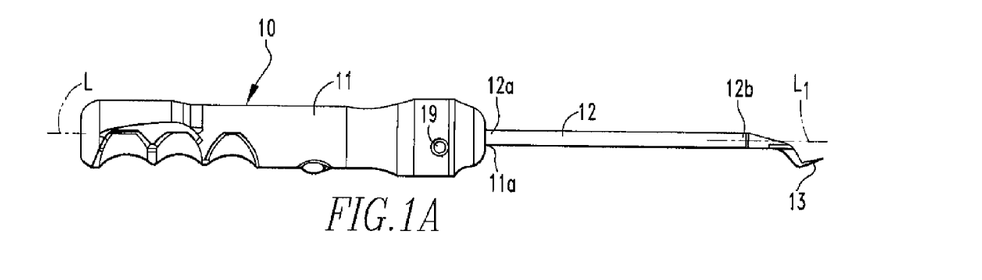
FIG. 1A shows a side view of a first embodiment of a surgical aimer of the present disclosure with the aimer located in an in-line position.
Figure 1B:
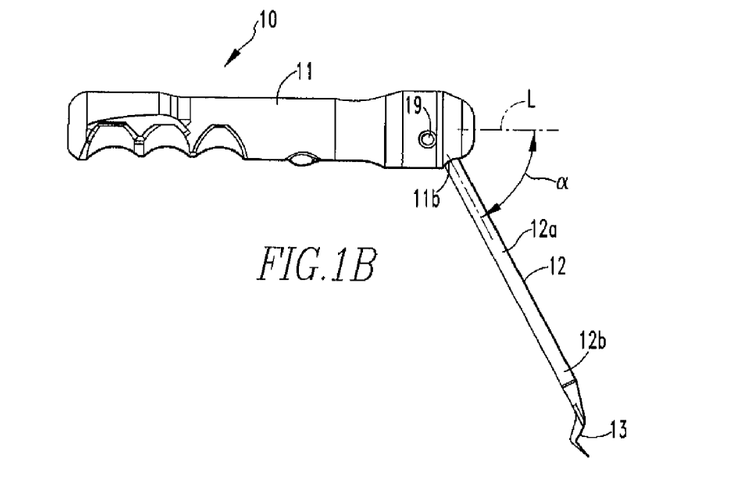
FIG. 1B shows a side view of a surgical aimer of FIG. 1A with the aimer located in a pistol grip position.

FIGS. 1A and 1B show the surgical aimer 10 of the present disclosure in an in-line position and a pistol grip position, respectively. The aimer 10 includes a handle 11 and a shaft 12 having a proximal portion 12a and a distal portion 12b, wherein the proximal portion 12a of the shaft 12 is coupled to the handle 11. In FIG. 1A, the shaft 12 is disposed within a first channel 11a that is parallel with a longitudinal axis L of the handle 11 and in FIG. 1B, the shaft 12 is disposed within a second channel 11b that is located at an angle a relative to the longitudinal axis of the handle 11. The distal portion 12b of the shaft 12 includes a tip 13 that is offset, between about 5 mm to about 7 mm, relative to a longitudinal axis $L_1$ of the shaft 12. The handle 11 also includes a mechanism 19 for coupling the handle 11 to the shaft 12, which will be further described below.

Figure 2A:
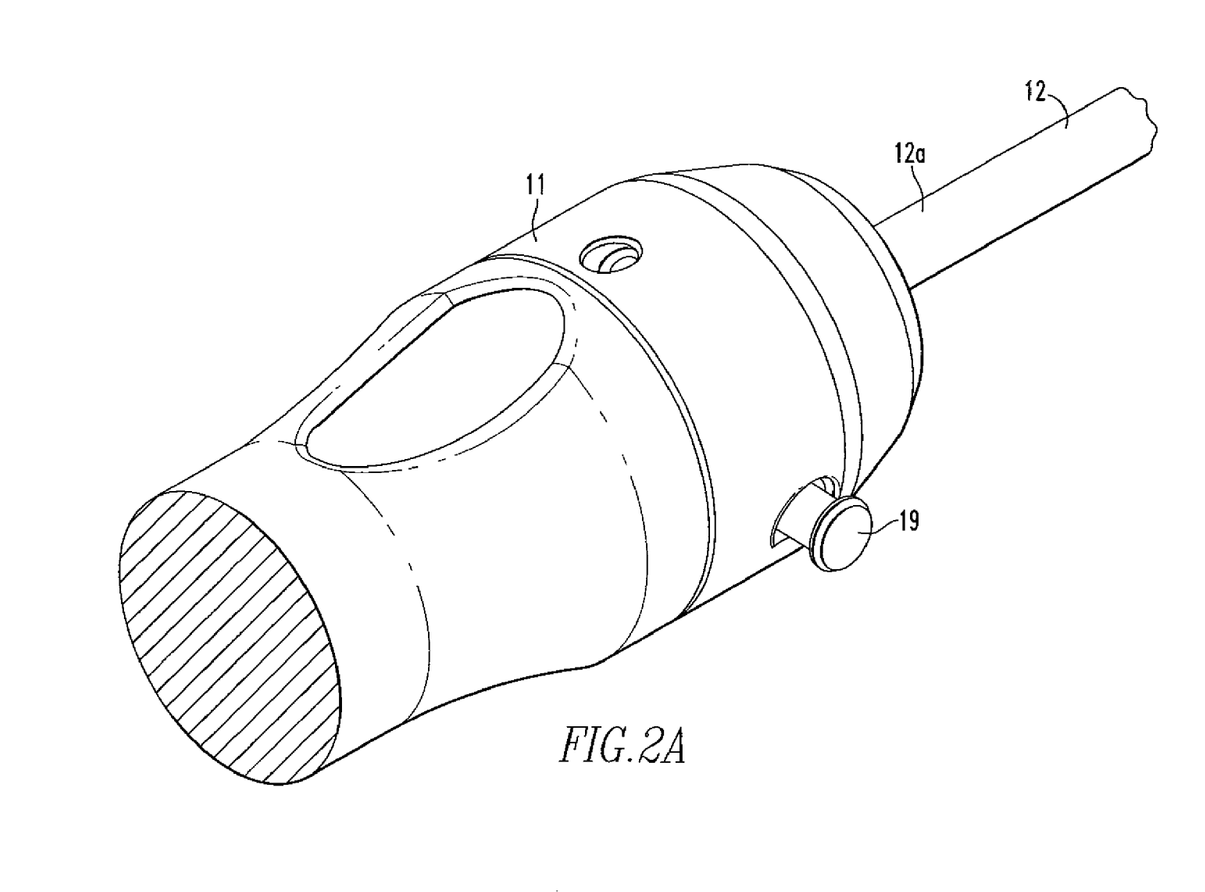
FIG. 2A shows a perspective view of the surgical aimer handle of the surgical aimer of FIG. 1A.
Figure 2B:
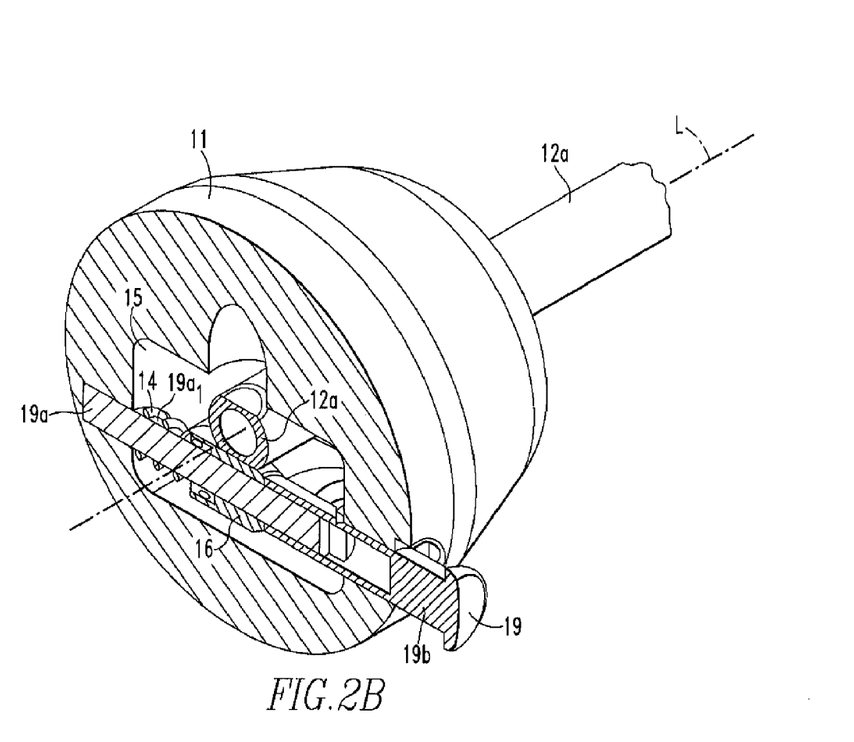
FIG. 2B shows a cross-sectional view of the surgical aimer handle of the surgical aimer of FIG. 1A.
Figure 2C:
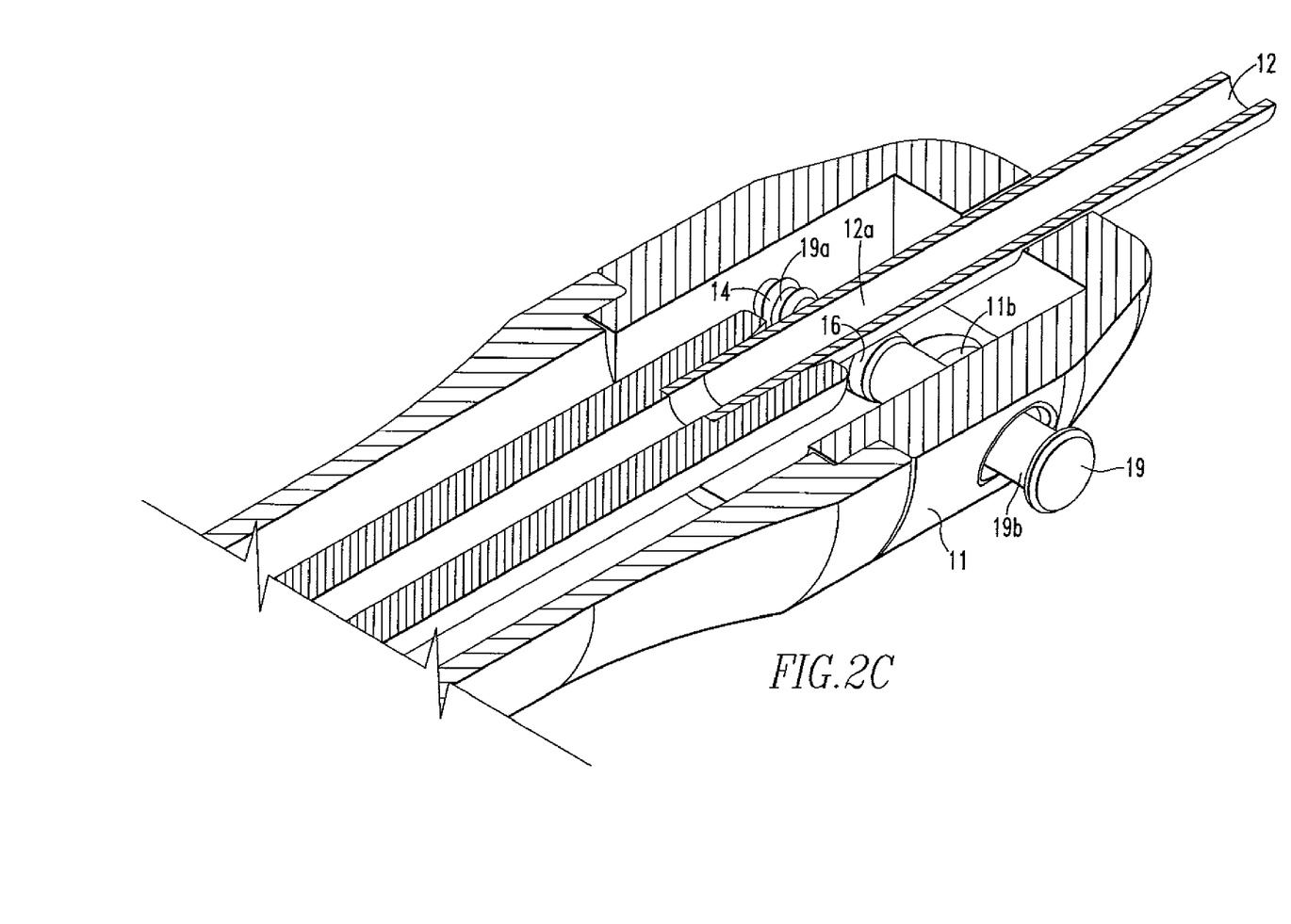
FIG. 2C shows a cross-sectional view of the surgical aimer handle and shaft of the surgical aimer of FIG. 1A.

FIGS. 2A, 2B, and 2C further show the mechanism 19 for coupling of the handle 11 to the shaft 12. As shown in FIG. 2B, the mechanism 19, which is transverse to the longitudinal axis L of the handle 11, includes a stationary member 19a and a movable member 19b slidably engaged with the stationary member 19a. A spring 14 is located on an outer surface $19a_1$ of the stationary member 19a between the movable member 19b and an inner wall 15 of the handle 11, such that the movable member 19b is spring-loaded against the stationary member 19a. The spring 14 is shown in an uncompressed state in FIGS. 2B and 2C. The movable member 19b includes a locking portion 16 that is engaged with the proximal portion 12a of the shaft 12 when the locking portion 16 is located in a first position, as shown in FIGS. 2B and 2C. However, when the mechanism 19 is activated such that the movable member compresses the spring 14 and the locking portion 16 is located in a second position, engagement between the proximal portion 12a of the shaft 12 and the locking portion 16 does not exist.

In use, the mechanism 19 is activated such that the locking portion 16 is located in a second position, as described above, the shaft 12a is disposed within the first channel 11a or the second channel 11b of the handle 11, and the mechanism 19 is then inactivated such that the locking portion 16 is located in a first position, as described above and shown in FIGS. 2B and 2C, to engage the shaft 12 and couple it to the handle 11. To uncouple the shaft 12 from the handle 11, the mechanism 19 is activated to locate the locking portion 16 in a second position, thereby disengaging the locking portion 16 from the shaft 12.

Figure 3:
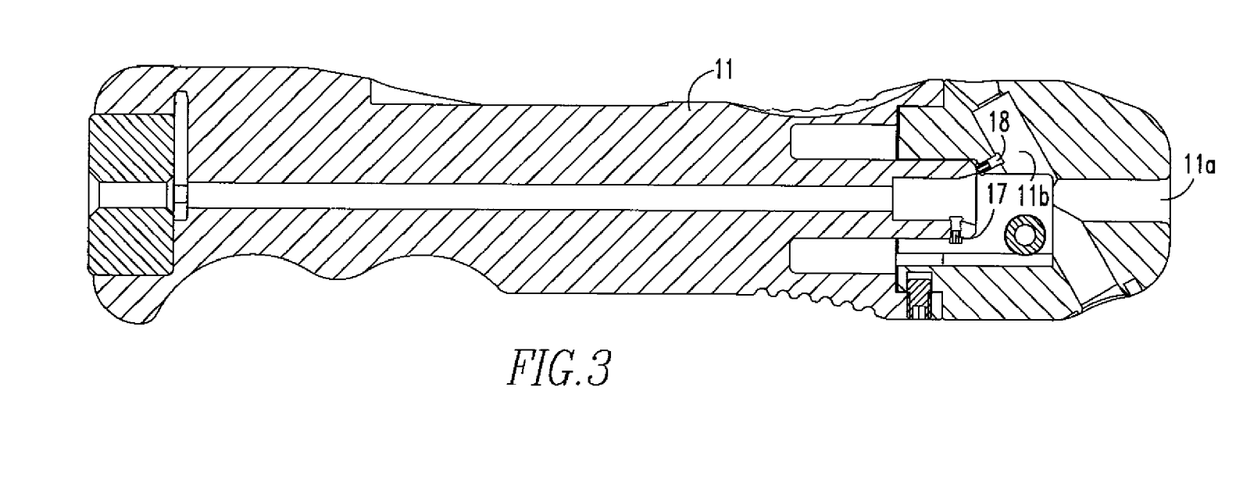
FIG. 3 shows the alignment pins of the surgical aimer handle of the surgical aimer of FIG. 1A.
Figures 4A, 4B:
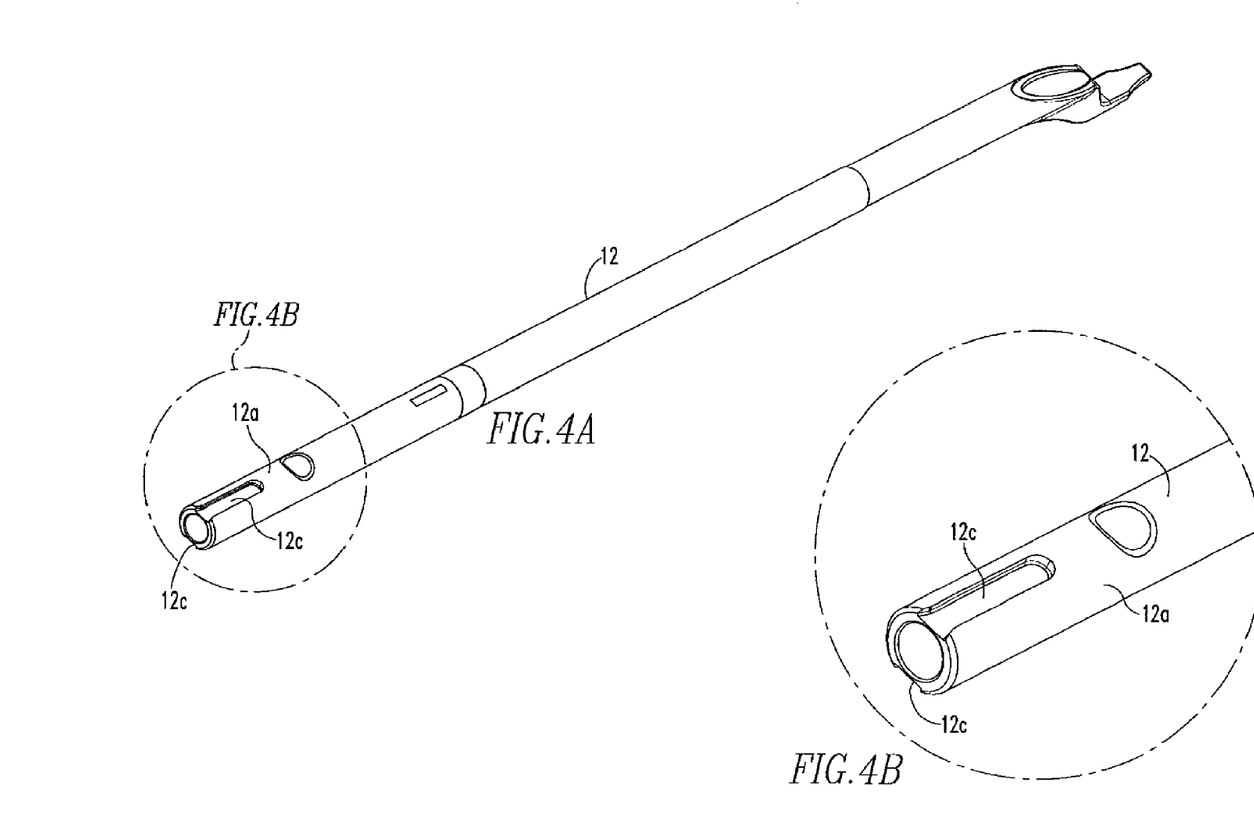
FIG. 4A shows an isometric view of the shaft of the surgical aimer of FIG. 1A.
FIG. 4B shows an enlarged view of the grooves of the shaft of FIG. 4A.

In addition to the locking portion 16 of the mechanism 19, FIG. 3 shows that the handle 11 also includes a first pin 17 for aligning the shaft 12 within the handle 11 when the shaft 12 is disposed within the first channel 11a and a second pin 18 for aligning the shaft 12 within the handle 11 when the shaft 12 is disposed within the second channel 11b. The pins 17, 18 slide within one of two grooves 12c located on the proximal end 12a of the shaft 12, as shown in FIGS. 4A and 4B, and engage the shaft 12 as the shaft 12 is disposed within the channels 11a, 11b. This engagement provides proper alignment of the shaft 12 within the channels 11a, 11b and therefore the handle 11.

Figure 5A:
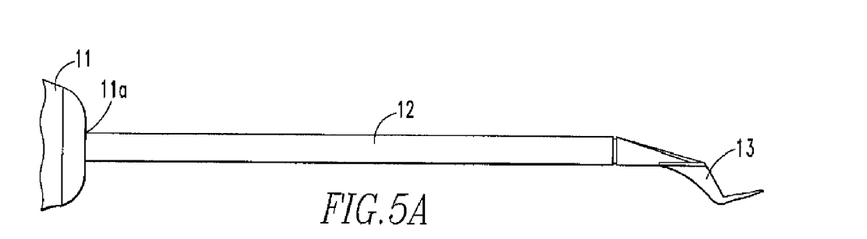
FIG. 5A shows a side view of the shaft of the surgical aimer of FIG. 1A having the tip positioned below the shaft.
Figure 5B:
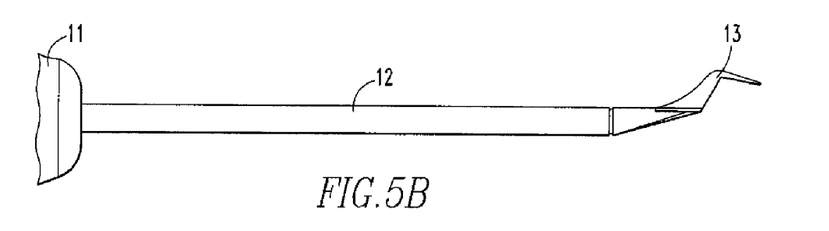
FIG. 5B shows a side view of the shaft of the surgical aimer of FIG. 1A having the tip positioned above the shaft.
Figure 6:
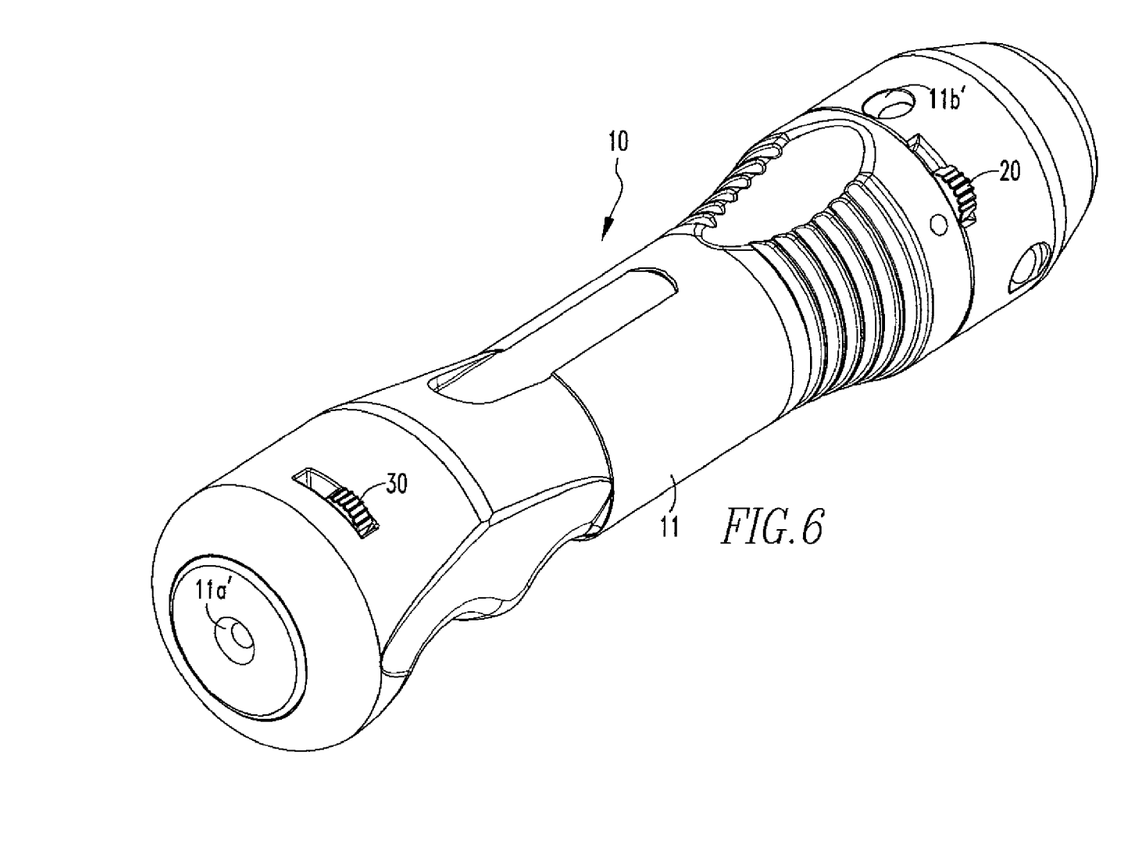
FIG. 6 shows an isometric view of the handle of a second embodiment of the surgical aimer of the present disclosure.
Figure 7:
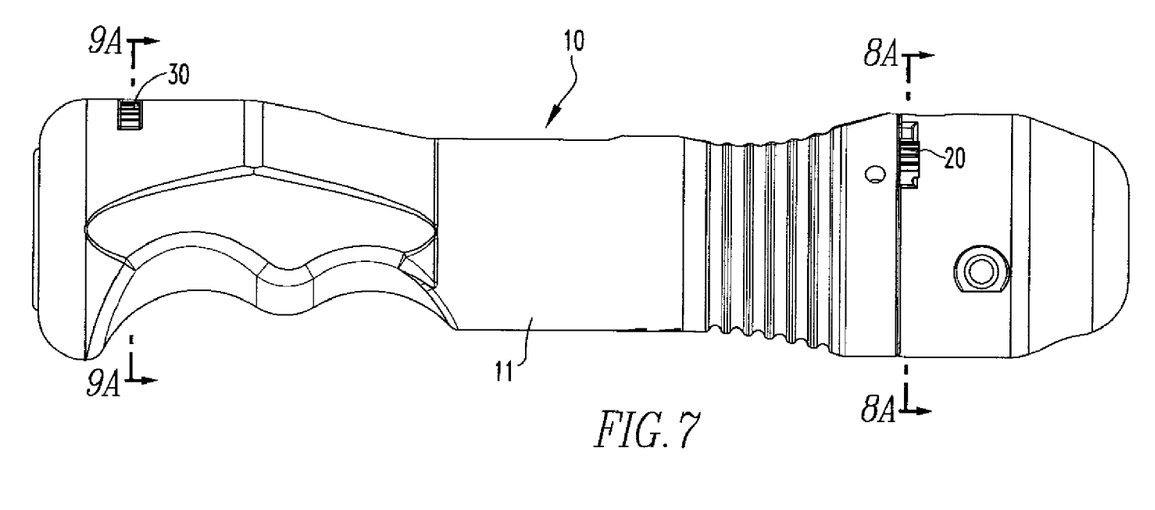
FIG. 7 shows a side view of the handle of the surgical aimer of FIG. 6.
Figure 8A:
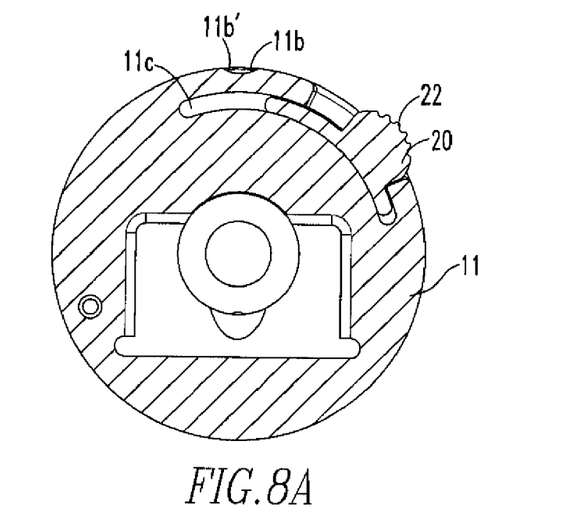
FIG. 8A shows cross-sectional view of the handle of FIG. 7 along line 8-8 with the first cover in a first position.
Figure 8B:
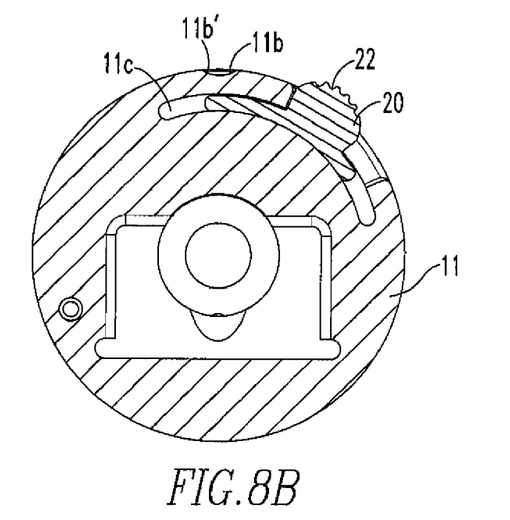
FIG. 8B shows a cross-sectional view of the handle of FIG. 7 along line 8-8 with the first cover in a second position.
Figure 9A:
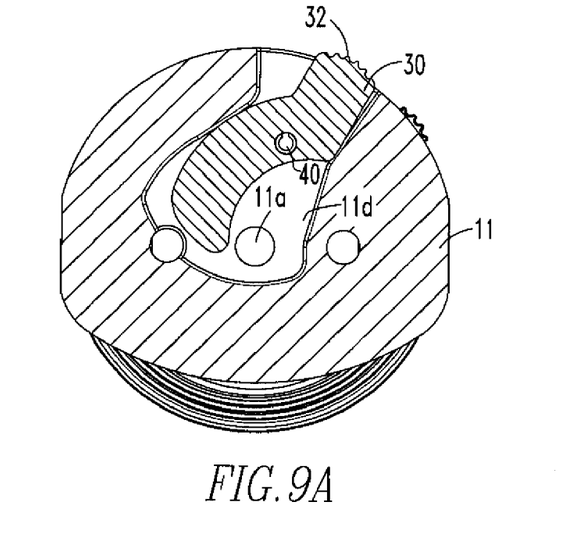
FIG. 9A shows a cross-sectional view of the handle of FIG. 7 along line 9-9 with the second cover in a first position.
Figure 9B:
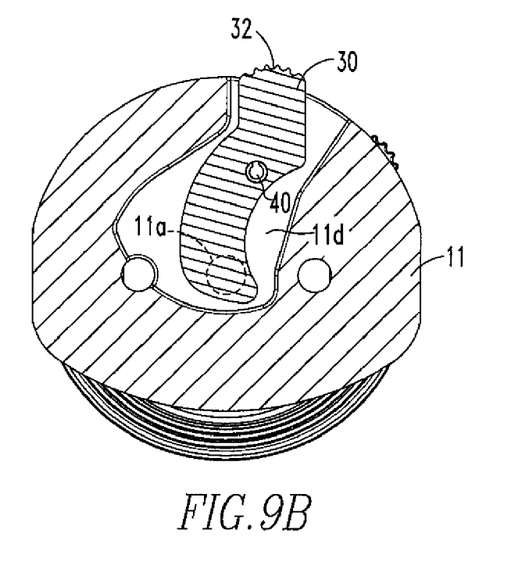
FIG. 9B shows a cross-sectional view of the handle of FIG. 7 along line 9-9 with the second cover in a second position.

As shown in FIGS. 5A and 5B, the shaft 12 may also be disposed within openings 11a, 11b such that the tip 13 is positioned below the shaft 12 or above the shaft 12, respectively. Having the tip 13 located below or above the shaft 12 is dependent on the required positioning and alignment of the shaft 12 for drilling of the graft tunnel in the femur. Regardless of the position of the tip 13, one of the two grooves 12c discussed above will engage with one of the pins 17, 18 to allow for proper alignment of the shaft 12.

Figure 10:
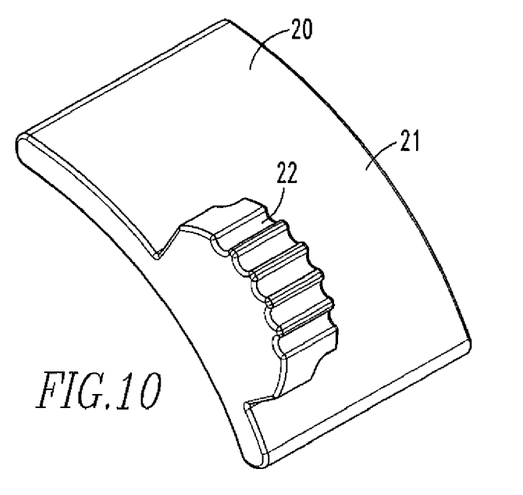
FIG. 10 shows a first cover for use with the handle of the surgical aimer of FIG. 6.
Figure 11:
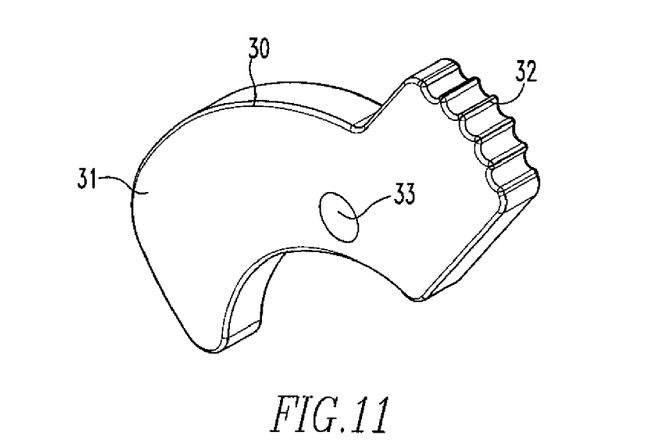
FIG. 11 shows a second cover for use with the handle of the surgical aimer of FIG. 6.

FIGS. 6-9 show a second embodiment of the surgical aimer 10 of the present disclosure. The handle 11 of the aimer 10 includes a first slidable cover 20 coupled to the handle 11 and a second slidable cover 30 coupled to the handle 11. As shown in FIGS. 10-11, the first and second covers 20, 30 both include a body 21, 31 having an actuating portion 22, 32 and the second cover 30 includes a through hole 33 for disposition of a fixation device, as will be further described below. As shown in FIGS. 8A and 8B, the first cover 20 is housed within a first aperture 11c such that in a first position, shown in FIG. 8A, the first cover 20 doesn't extend over the second channel 11b and in a second position, shown in FIG. 8B, the first cover 20 does extend over the second channel 11b. Similarly, as shown in FIGS. 9A and 9B, the second cover 30 is housed within a second aperture 11d such that in a first position, shown in FIG. 9A, the second cover 30 doesn't extend over the first channel 11a and in a second position, shown in FIG. 9B, the second cover 30 does extend over the first channel 11a. The second cover 30 is coupled to the handle 11 via a fixation device 40, such as a screw, or other fixation device that couples the cover 30 to the handle 11, but still allows movement of the cover 30 between the first and second positions.

During use of the aimer 10 in a surgical procedure, the first and second covers 20, 30 are located in their second positions in order to substantially reduce the possibility of blood and fluid from flowing out of openings 11a', 11b' and thereby causing possible contamination. The user can slide the covers 20, 30 between the first and second positions by applying pressure to the actuating portions 22, 32, which causes the cover to move from one position to another position.

The handle 11 can be used in a full range of shafts and other devices that require optional positioning. The shafts 12 may range in a variety of sizes. The aimer is 10 manufactured using medical grade materials and standard machine processes. For example, the handle 11 is made from Radel and the shaft 12 and tip 13 are made from stainless steel. However, other medical grade materials may be used. The covers 20, 30 may be of a different shape than what is shown in FIGS. 10 and 11. The actuating portions 22, 32 include knurled surfaces for easier grip and movement of the covers 20, 30. However, other surface features may be used on the portions 22, 32.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A surgical aimer comprising:
   a shaft, the shaft including a proximal portion and a distal portion; and
   a handle coupled to the proximal portion of the shaft, the handle including:
   a mechanism for coupling the handle to the shaft and releasing the handle from the shaft, the mechanism being disposed transverse to a longitudinal axis of the handle,
   an inner wall,
   a first channel configured for disposal of the shaft, and
   a second channel configured for disposal of the shaft, the first channel being parallel with the longitudinal axis of the handle and the second channel being located at an angle relative to the first channel,
   wherein the mechanism includes:
   an elongated movable member having an outer surface and an at least partially hollow core, the outer surface of the elongated movable member having a locking portion disposed thereon;
   an elongated stationary member having an outer surface, the elongated stationary member being partially disposed in the hollow core of the elongated movable member, the elongated movable member being slidably engaged over the elongated stationary member partially disposed in the hollow core and the elongated movable member being spring-loaded against the elongated stationary member; and
   a resilient member disposed along the outer surface of the elongated stationary member between the elongated movable member and the inner wall of the handle, wherein the resilient member is configured to be movable from an uncompressed state to a compressed state upon sliding movement of the elongated movable member over the elongated stationary member the locking portion being located h a first position relative to the first and second channels when the resilient member is in the uncompressed state, the locking portion being moved to a second position relative to the first and second channels when the resilient member is moved to the compressed state, and
   wherein the locking portion is operative while the shaft is disposed in the first channel and while the shaft is disposed in the second channel, to be engaged with the proximal portion of the shaft when in the first position, thereby coupling the handle to the shaft, and to be disengaged from the proximal portion of the shaft when in the second position, thereby releasing the handle from the shaft;
   wherein the shaft is parallel with the longitudinal axis of the handle when the shaft is disposed within the first channel; and
   wherein the shaft is located at an angle relative to the longitudinal axis of the handle when the shaft is disposed within the second channel.

2. The surgical aimer of claim 1 wherein the mechanism includes a stationary member and a movable member, the movable member slidably engaged with the stationary member.

3. The surgical aimer of claim 2 wherein the stationary member includes a spring, the movable member being spring-loaded against the stationary member.

4. The surgical aimer of claim 2 wherein the movable member includes a locking portion.

5. The surgical aimer of claim 4 wherein the locking portion is engaged with the proximal portion of the shaft when the locking portion is located in a first position and unengaged with the proximal portion of the shaft when the locking portion is located in a second position.

6. The surgical aimer of claim 1 wherein the handle includes a first pin for aligning the shaft within the handle when the shaft is disposed within the first channel and a second pin for aligning the shaft within the handle when the shaft is disposed within the second channel.

7. The surgical aimer of claim 1 wherein the distal portion of the shaft includes a tip, the tip being offset at an angle relative to the shaft.

8. The surgical aimer of claim 7 wherein the tip is positioned above the shaft.

9. The surgical aimer of claim 7 wherein the tip is positioned below the shaft.

10. A surgical aimer handle comprising:
    a mechanism configured for coupling and uncoupling the handle to a shaft.

11. The surgical aimer handle of claim 10 wherein the handle includes a first pin for aligning the shaft within the handle when the shaft is disposed within the first channel and a second pin for aligning the shaft within the handle when the shaft is disposed within the second channel.

12. The surgical aimer handle of claim 10 wherein a distal portion of the shaft includes a tip, the tip being offset at an angle relative to the shaft.

13. The surgical aimer handle of claim 12 wherein the tip is positioned above the shaft.

14. The surgical aimer handle of claim 12 wherein the tip is positioned below the shaft.

15. The surgical aimer of claim 1 wherein the handle includes a first cover slidably coupled to the handle and a second cover slidably coupled to the handle.

16. The surgical aimer of claim 15 wherein the first cover is configured for extending over the second channel and the second cover is configured for extending over the first channel.

17. The surgical aimer handle of claim 10 wherein the handle includes a first cover slidably coupled to the handle and a second cover slidably coupled to the handle.

18. The surgical aimer handle of claim 17 wherein the first cover is configured for extending over the second channel and the second cover is configured for extending over the first channel.

19. The surgical aimer of claim 15 wherein both the first cover and the second cover comprise a body and an actuating portion.

20. The surgical aimer of claim 17 wherein both the first cover and the second cover comprise a body and an actuating portion.

21. The handle of claim 19 further comprising:
   wherein, upon actuation of the actuating portion of the first cover, the body of the first cover is configured to slideably extend over the first channel, and
   wherein, upon actuation of the actuating portion of the second cover, the body of the second cover is configured to slideably extend over the second channel.

* * * * *